United States Patent [19]

Mori

[11] Patent Number: 4,676,956
[45] Date of Patent: Jun. 30, 1987

[54] APPARATUS FOR PHOTOSYNTHESIS

[76] Inventor: Kei Mori, 3-6-3-501, Kaminoge, Setagaya-ku, Tokyo, Japan

[21] Appl. No.: 563,909

[22] Filed: Dec. 21, 1983

[30] Foreign Application Priority Data

Dec. 24, 1982 [JP] Japan ................... 57-232271
Dec. 24, 1982 [JP] Japan ................... 57-232272
Dec. 31, 1982 [JP] Japan ................... 57-230790

[51] Int. Cl.$^4$ .......... A01G 7/02; F21V 33/00; C12M 1/04; C12M 1/36
[52] U.S. Cl. .................... 422/186; 47/1.4; 60/272; 250/435; 261/87; 261/124; 362/101; 422/23; 422/24; 422/80; 435/289; 435/313; 435/315
[58] Field of Search ............ 362/101; 422/186, 23, 422/904, 24, 80, 143; 60/272, 274, 275; 47/1.4; 435/287, 257, 173, 313, 813, 315, 289, 29, 314, 819; 261/87, 114 VT, 121 R, 124; 250/435, 436; 350/96.15

[56] References Cited

U.S. PATENT DOCUMENTS

| | | | |
|---|---|---|---|
| 2,609,277 | 9/1952 | McNamara | 261/114 VT |
| 2,658,310 | 10/1953 | Cook | 435/257 |
| 2,777,677 | 1/1957 | Bunch | 261/121 R |
| 2,815,607 | 12/1957 | Schroeder | 435/257 |
| 3,400,051 | 9/1968 | Hofschneider | 435/315 |
| 3,782,701 | 1/1974 | Hunt | 261/121 R |
| 3,955,317 | 5/1976 | Gudin | 47/1.4 |
| 3,955,318 | 5/1976 | Hulls | 47/1.4 |
| 3,959,923 | 6/1976 | Selke | 47/1.4 |
| 3,986,297 | 10/1976 | Ichimura et al. | 47/1.4 |
| 4,235,043 | 11/1980 | Harasawa et al. | 47/1.4 |
| 4,253,271 | 3/1981 | Raymond | 47/1.4 |
| 4,320,594 | 3/1982 | Raymond | 47/1.4 |
| 4,324,068 | 4/1982 | Anthony | 47/1.4 |
| 4,473,970 | 10/1984 | Hills | 47/1.4 |
| 4,495,549 | 1/1985 | Carlson et al. | 362/101 |

FOREIGN PATENT DOCUMENTS

| | | | |
|---|---|---|---|
| 3118581 | 10/1978 | Japan | 435/313 |
| 0121789 | 7/1983 | Japan | |
| 0000282 | 5/1979 | PCT Int'l Appl. | |
| 1335546 | 12/1971 | U.S.S.R. | 47/1.4 |
| 0505405 | 5/1976 | U.S.S.R. | 47/1.4 |

Primary Examiner—Stephen J. Lechert, Jr.
Assistant Examiner—Howard J. Lacker
Attorney, Agent, or Firm—Jordan and Hamburg

[57] ABSTRACT

An apparatus for photosynthesis includes a unique arrangement for supplying light and $CO_2$-containing air to a reaction chamber in a sure and stable manner. The reaction chamber is irradiated for photosynthesis from the inside and/or outside thereof in an intermittent mode. $CO_2$-containing air is routed from a $CO_2$ source to a rotatable disc which is positioned in a bottom portion of the apparatus. Part of the $CO_2$-containing air is ejected sideways from the disc to cause it into rotation, while the rest of the air is ejected upwardly into the reaction chamber. The reaction chamber is partitioned into a plurality of compartments which are sequentially supplied with the $CO_2$-containing air in accordance with the rotation of the disc.

21 Claims, 16 Drawing Figures

APPARATUS FOR PHOTOSYNTHESIS

BACKGROUND OF THE INVENTION

The present invention relates to an apparatus for photosynthesis and, more particularly, to an arrangement for allowing light and carbon dioxide ($CO_2$) to be supplied thereto in an even and effective manner.

Photosynthetic apparatuses heretofore proposed include an apparatus for culturing chlorella (unicellular microorganism containing chlorophyl). Difficulty experienced in culturing chlorella is that illumination with intensities higher than a certain level destructs the chlorophyl and produces a toxin (phaeophobite) while illumination with intensities lower than a certain level fails to cause photosynthesis altogether. It is therefore a primary requisite for effective photosynthesis that all the cells containing a photosynthetic substance be constantly supplied with light in even distribution. An ideal situation is, therefore, that a photosynthetic substance be passed through a very narrow clearance while a predetermined intensity of light is directed perpendicular to the clearance. Then, sufficient light will be evenly applied to all the cells containing the photosynthetic substance with a minimum of attenuation and without any change in its wavelength component. Meanwhile even supply of a sufficient amount of $CO_2$ all over the reaction bath is essential in attempting efficient photosynthesis.

The applicant has proposed an apparatus for photosynthetic reaction in various forms contemplated to implement the demands discussed above. The present invention constitutes a further improvement over the precedent implementations.

SUMMARY OF THE INVENTION

It is an object of the present invention to provide an apparatus for photosynthesis which effectively supplies light into a reaction bath for photosynthetic reactions.

It is another object of the present invention to provide an apparatus for photosynthesis which communicates $CO_2$-containing air to a reaction bath in a sure and stable manner.

It is another object of the present invention to provide an apparatus for photosynthesis which is furnished with a simple and economical device for producing $CO_2$.

It is another object of the present invention to provide a generally improved apparatus for photosynthesis.

An apparatus for photosynthesis of the present invention comprises a reaction bath for causing a photosynthetic reaction therein, a plurality of narrow tubular photoradiators arranged upright in the reaction bath parallel to each other, each of the photoradiators radiating light which propagates therethrough, and a disc rotatable in a horizontal plane below and perpendicular to the photoradiators, the disc being formed with horizontal passageways for ejecting jets of nitrogen oxide-containing air, and vertical passageways for ejecting jets of carbon dioxide-containing air toward gaps defined between the adjacent photoradiators, the horizontal passageways being oriented to apply a moment of a force which tends to rotate the disc about an axis thereof, whereby the disc is caused to rotate while supplying the carbon dioxide-containing air into the reaction bath via the vertical passageways.

In accordance with the present invention, an apparatus for photosynthesis includes a unique arrangement for supplying light and $CO_2$-containing air to a reaction chamber in a sure and stable manner. The reaction chamber is irradiated for photosynthesis from the inside and/or outside thereof in an intermittent mode. $CO_2$-containing air is routed from a $CO_2$ source to a rotatable disc which is positioned in a bottom portion of the apparatus. Part of the $CO_2$-containing air is ejected sideways from the disc to cause it to rotate, while the rest of the air is ejected upwardly into the reaction chamber. The reaction chamber is partitioned into a plurality of compartments which are sequentially supplied with the $CO_2$-containing air in accordance with the rotation of the disc.

The above and other objects, features and advantages of the present invention will become apparent from the following detailed description taken with the accompanying drawings.

BRIEF DESCRIPTION OF THE DRAWINGS

FIG. 11 is a fragmentary section of another embodiment of the present invention;

DESCRIPTION OF THE PREFERRED EMBODIMENTS

While the apparatus for photosynthesis of the present invention is susceptible of numerous physical embodiments, depending upon the environment and requirements of use, substantial numbers of the herein shown and described embodiments have been made, tested and used, and all have performed in an eminently satisfactory manner.

To facilitate understanding of the present invention, a reference will be made to an apparatus for photosynthesis which the applicant has proposed.

Figure 1:
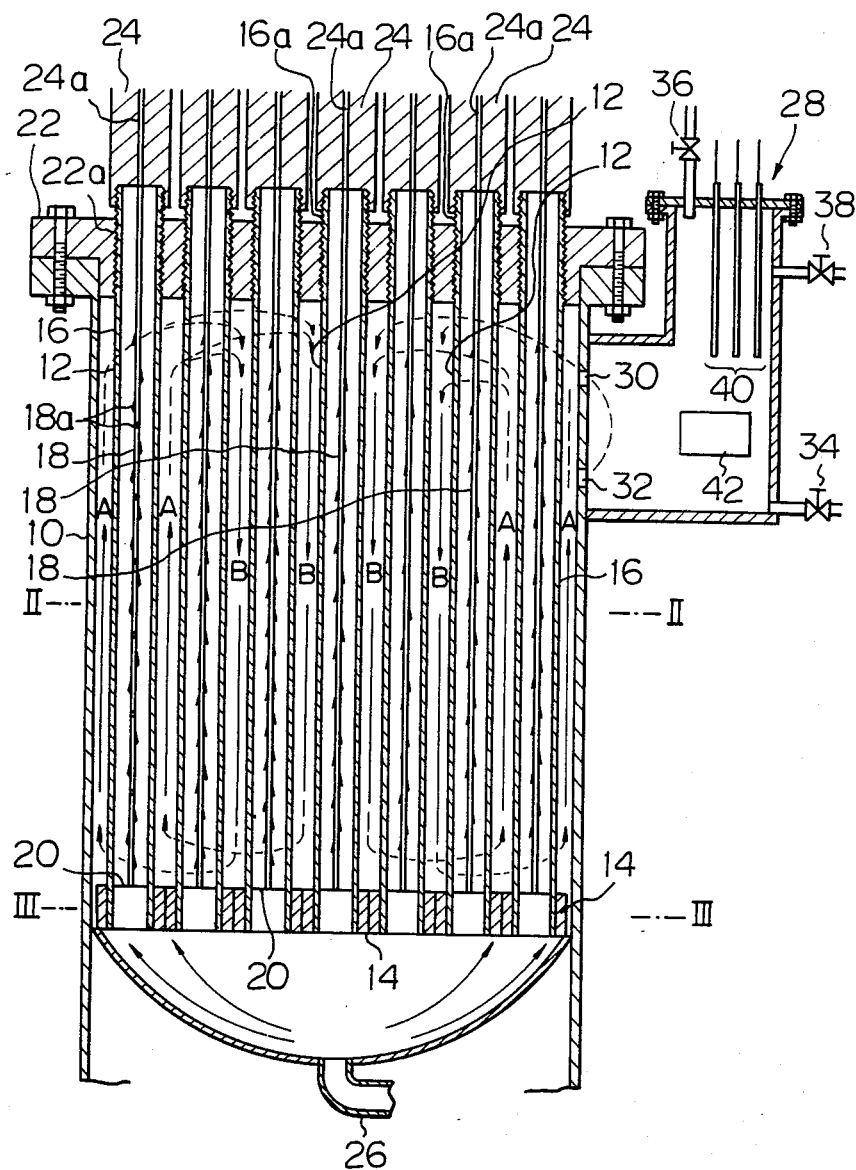
FIG. 1 is a sectional side elevation of a apparatus for photosynthesis previously proposed by the applicant.
Figure 2:
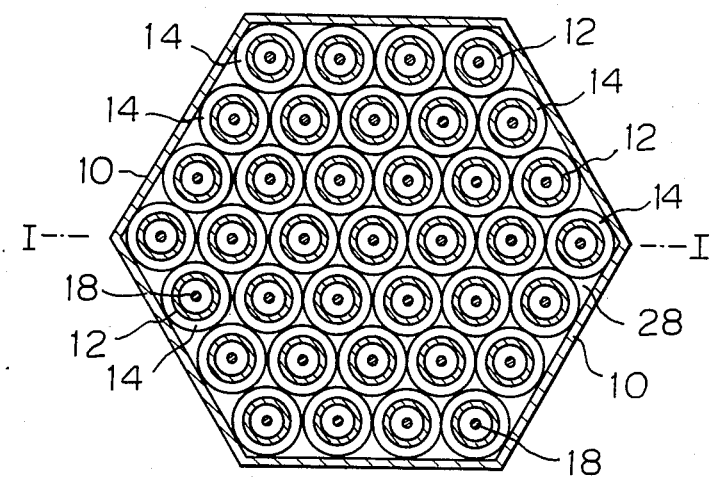
FIG. 2 is a section along line II—II of FIG. 1.
Figure 3:
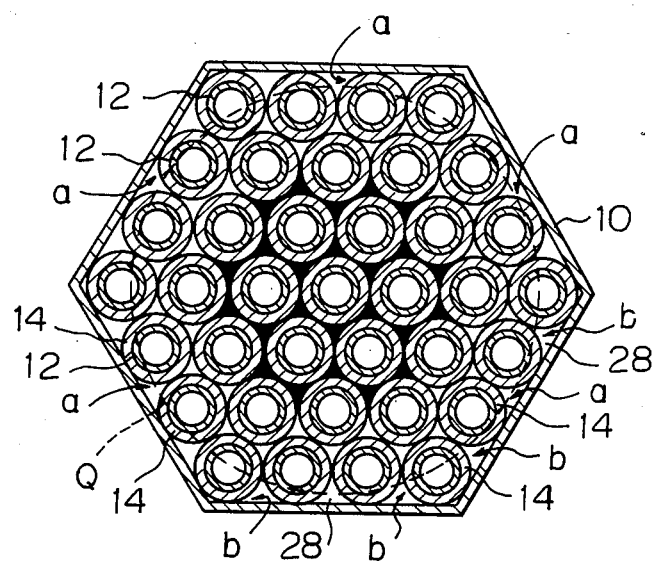
FIG. 3 is a section along line III—III of FIG. 1.

Referring to FIGS. 1–3, the apparatus includes a reaction bath generally designated by the reference numeral 10. A number of photoradiators 12 in the form of narrow tubes are arranged upright and in parallel with each other within the reaction bath 10. Each of the photoradiators 12 is rigidly fit in a short tube 14 at its lower end in a fluid tight manner. The photoradiator 12 comprises a transparent tube or sheath 16, an optical rod 18 and a mirror 20 located at a lower end portion of each photoradiator 12. A lid 22 removably covers the top of the reaction bath 10 and has threaded openings 22a in which threaded upper portions 16a of the respective tubes 16 are engaged. Thus, when the lid 22 is removed from the reaction bath 10, it is accompanied by the photoradiators 12 to facilitate cleaning of the reaction bath 10 or the photoradiators 12. Fiber optic cables 24 are in threaded engagement respectively with the upper end of the threaded portions 16a of the tubes 16 at their light output ends. In this position of each cable 24, its optical fiber 24a is aligned at its end with the end of the optical rod 18 in the associated photoradiator 12, so that the light propagating through the optical fiber 24a is effectively transferred to the optical rod 18.

Each optical rod 18 is made of quartz, plastics or the like. The rod 18 carries thereon a light diffusing material 18a at desiredly spaced locations along its length. The light diffusing material 18a has a refractive index which is larger then that of quartz or plastics, thereby causing the light to break through the material 18a out of the rod 18.

A conduit 26 is communicated with the reaction bath 10 to supply $CO_2$-containing air thereinto. As shown in FIG. 3, the short tubes 14 in which the lower ends of the photoradiators 12 are fit are bonded together at their outer surfaces while defining gaps 28 therebetween. The gaps 28 are stopped up in a central area of the reaction bath 10 (black gaps 28 in FIG. 3). $CO_2$-containing air fed into the reaction bath 10 by the conduit 26 flows through the open gaps 28 adjacent to the periphery of the bath 10, advances upward through the spaces between the photoradiators 12 as indicated by arrow A in FIG. 1, flows toward the center of the bath 10 at the upper end of the latter, flows down along the center as indicated by arrows B, and is then redirected by the closed gaps 28 in the central area toward the periphery of the reaction bath 10, thus recirculating within the reaction bath 10. With this arrangement, the recirculating air moves at a substantial velocity along the outer periphery of each photoradiator 12 while entraining the culture medium, thereby preventing the photosynthetic substance from becoming deposited on the photoradiators 12. This frees the output light of the photoradiators 12 from interception to thereby supply all the photosynthetic substance with optical energy and $CO_2$ each in an even distribution.

It will be seen in the above construction that, if the area is made smaller at the region where the air flows downward than at the region where the air flows upward, the velocity of water will be increased at the downward flow region to minimize contamination to the photoradiators 12 in this region. While the gaps 28 in the central area of the bath 10 are stopped up, those in the peripheral area may be stopped up instead.

An auxiliary bath 28 is mounted on an upper side portion of the reaction bath 10 and communicated with the latter through openings 30 and 32 which are located one above the other. A valve 34 is positioned in the vicinity of the lower end of the auxiliary bath 28 so as to discharge the product of photosynthesis from the apparatus. A second valve 36 is mounted on the top of the auxiliary bath 28. This valve 36 is operable to supplement the culture medium and pH control solution to make up for the shortage which results from the discharge of the product through the valve 34. A third valve 38 is mounted on an upper side portion of the auxiliary bath 28 in order to controllably let the air out of the reaction bath 10 to control the pressure inside the reaction bath 10. Where use is made of a pressure regulating valve as the valve 38 for automatically controlling the bath pressure to a reference level, the $CO_2$ concentration in the water can be increased to promote photosynthesis and, at the same time, the pressure in the reaction bath 10 is prevented from lowering to change $CO_2$ into $M^IHCO_3$. Disposed inside the auxiliary bath 28 are various instruments 40 for monitoring the photosynthetic reaction in the reaction bath 10, e.g. thermometer, pressure gauge, pH meter and densitometer. The conditions inside the reaction bath 10 are so controlled as to effect photosynthesis in an optimum manner in response to outputs of such instruments. For example, the temperature in the reaction bath 10 may be controlled by controlling a heat generating/absorbing device 42 which is positioned in the auxiliary bath 28. Also, the outputs of the instruments are processed to notify the timing to collect the product.

As long as the photosynthetic reaction is to be carried out without interruption, the product will be collected through the auxiliary bath 28. When interruption of the reaction is permissible, the end (not shown) of the conduit 26 may be communicated to a vacuum source (not shown) or the like instead of the $CO_2$-containing air supply, so that the product can be controlled through the conduit 26.

Figure 4:
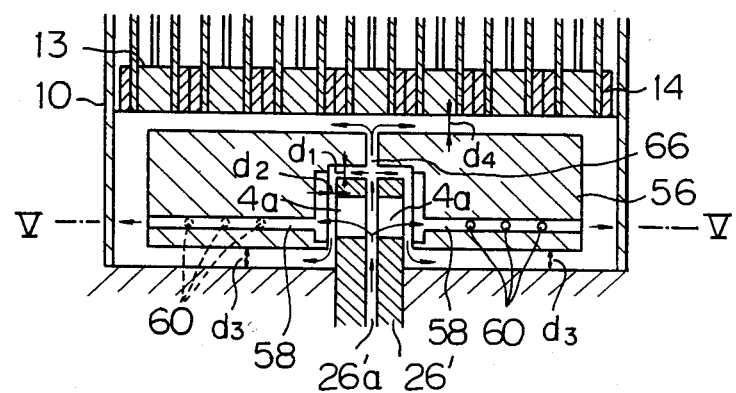
FIG. 4 is a fragmentary section of another apparatus for photosynthesis previously proposed by applicant.
Figure 5:
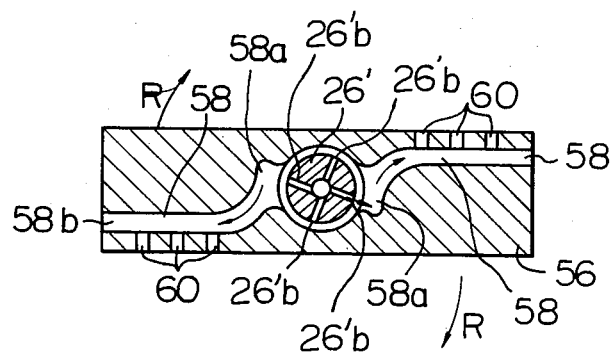
FIG. 5 is a section along line V—V of FIG. 4.

Another apparatus the applicant has proposed is shown in FIGS. 4 and 5. In these drawings, the same structural elements as those shown in FIGS. 1–3 are designated by the same reference numerals. The conduit 26 (FIG. 1) has an extension 26′ which protrudes into the reaction bath 10 to a position below the photoradiators 12. The conduit extension 26′ is shaped at its upper end portion to have an axial passageway 26′a and a plurality of radial passageways 26′b which extend obliquely and radially outwardly from the axial passageway 26′a. A rotor 56 is movably coupled over the top of the conduit extension 26′. The rotor 56 is formed with passageways 58 and a plurality of air ejection ports 60 which extend throughout the rotor 56 from each of the passageways 58, as illustrated.

In operation, air fed through the axial passageway 26′a of the conduit extension 26′ is discharged from the radial passageways 26′b to impinge on side wall portions 58a of the respective passageways 58, thereby giving the rotor 56 the tendency to rotate clockwise as indicated by arrows R in FIG. 5. The air passed through the passageways 58 is ejected from the ejection ports 60 to drive the rotor 56 in the direction R. The rotor 56 is caused to float by the air coming out through the upper end of the axial passageway 26′a of the conduit extension 26′, a clearance $d_1$ thus developing between the upper end of the conduit extension 26′ and the rotor 56. This part of the air, therefore, flows radially outward through the clearance $d_1$ as indicated by arrows in FIG. 4. Meanwhile, the air flowing through the gap $d_1$ and the air discharged from the radial passageways 26′b is partly routed through an annular clearance $d_2$ between the outer surface of the conduit extension 26′ and the inner wall of the rotor 30 into a clearance $d_3$ between the bottom of the rotor 56 and the bottom of the reaction bath 10. As a result, the air streams in the clearance $d_1$ and $d_3$ serve as an air cushion for supporting the rotor 56 while the air stream in the clearance $d_2$ functions as an air bearing for rotatably supporting the rotor 56. The major torque acting on the rotor 56 is created by the air jets from the ejection ports 60. If desired, the rotor 56 may be formed with a through upward passageway 66 to pass the air into a clearance $d_4$ between the bottoms of the photoradiators 12 and the top of the rotor 56. The air stream in this clearance $d_4$ will more effectively air-cushion the rotor 56 in cooperation with the other air streams.

Figure 6:
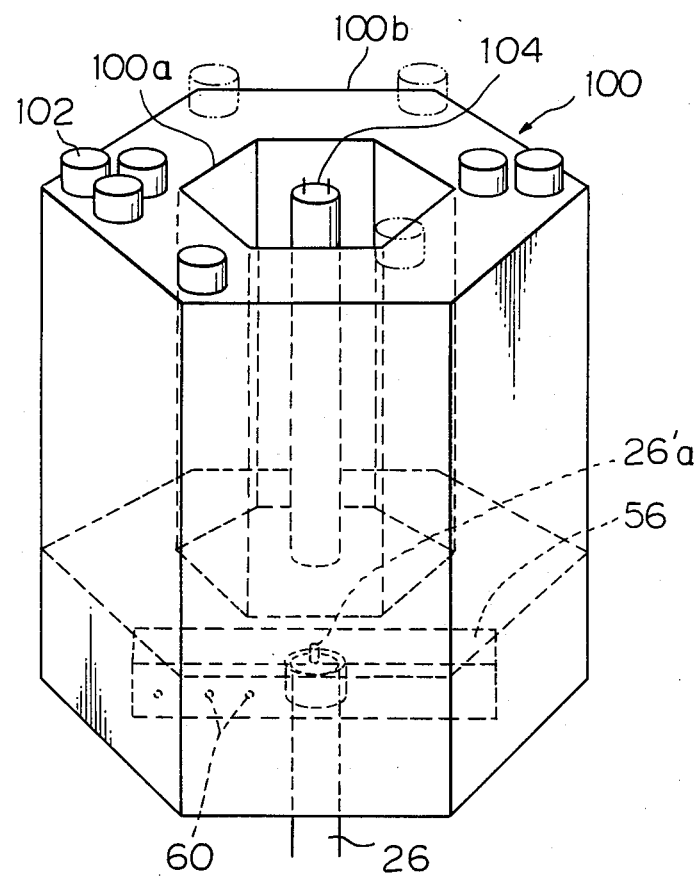
FIG. 6 is a schematic perspective view of an apparatus for photosynthesis embodying the present invention.
Figure 7:
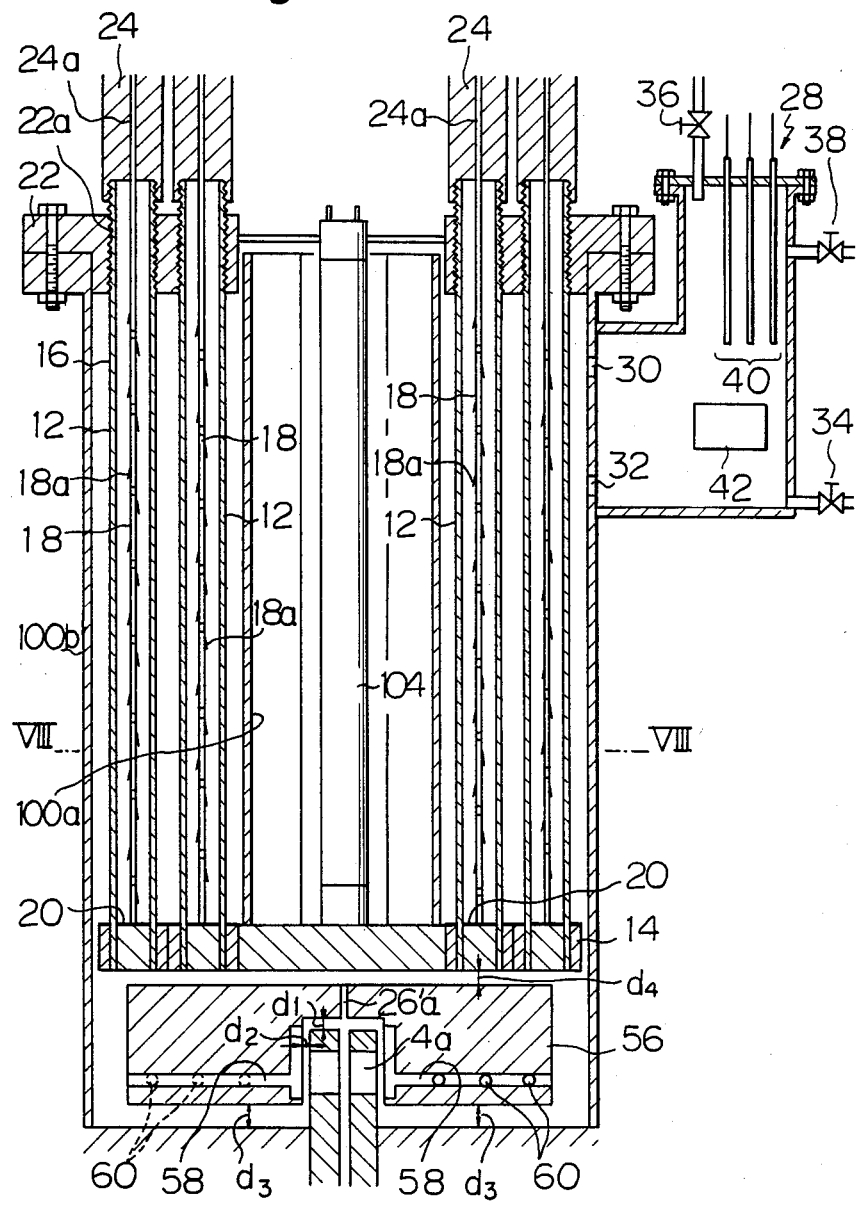
FIG. 7 is a sectional side elevation of the apparatus shown in FIG. 6.
Figure 8:
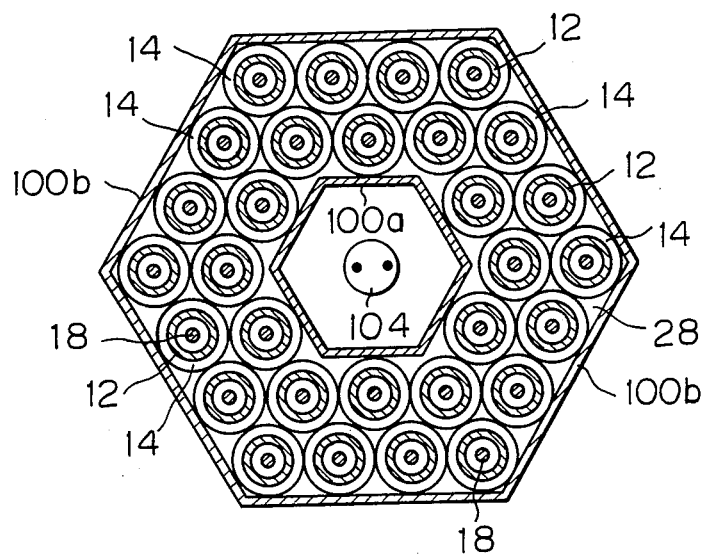
FIG. 8 is a section along line VIII—VIII of FIG. 7.

Referring to FIGS. 6–8, an apparatus for photosynthesis embodying the present invention is shown and includes a reaction bath 100. The reaction bath 100 is defined by an inner transparent wall 100a and an outer transparent wall 100b which surrounds the inner wall 100a. A number of photoradiators 102 are arranged side by side in the generally annular space defined between the inner and outer transparent walls 100a and 100b. Each photoradiator 102 is constructed essentially in the same manner as the photoradiators of the applicant's previously proposed apparatuses. A light source or lamp 104 is disposed at the center of the reaction bath, i.e., inwardly of the inner wall 100a, parallel to the photoradiators 102. In this construction, light emanating from the lamp 104 will be transmitted through the inner transparent wall 100a into the reaction bath 100 to cause photosynthetic reactions of a desired substance to occur therein.

Figure 9:
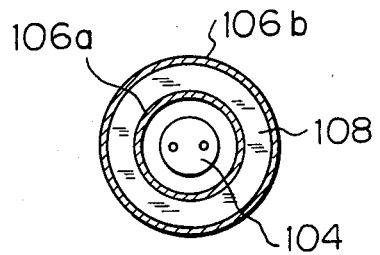
FIG. 9 is a fragmentary sectional plan view of a modification to the embodiment shown in FIGS. 6–8.

Concerning the lamp 104, it may comprise a fluorescent lamp or a xenon lamp by way of example. Where a xenon lamp is selected, it is a primary requisite to prevent ultraviolet and infrared rays issuing from the lamp from entering the reaction bath. An implementation available for intercepting such undesired rays is, as shown in FIG. 9, disposing coaxial inner and outer tubes 106a and 106b around the lamp 104, and filling the annular space between the tubes 106b with water or the like 108. The tubes 106a and 106b are commonly made of a transparent material which does not transmit ultraviolet rays. The water 108 serves to absorb infrared rays.

If necessary, the reaction bath 100 may be designed for outdoor use or the lamp 104 may be positioned outwardly of the outer wall 100b. In such a case, even the light from the external light source such as the sun will be transmitted through the outer wall 100b into the reaction bath 100 contributing to the photosynthetic reaction. The availability of light from both the inside and outside of the reaction bath for photosynthetic reactions is desirable from an efficiency standpoint.

The reaction bath 100 may be supplied with $CO_2$-containing air by the same construction which has been discussed with reference to FIGS. 4 and 5. As shown, the $CO_2$-containing air supply arrangement is disposed below the reaction bath 100 and includes the conduit 26 with the axial passageway 26'a and the rotor 56 with the ejection ports 60. The rest of the construction is similar to that of the prior art one previously proposed by the applicant and, therefore, the same structural elements thereof are designated by the same reference numerals.

As well known in the art, it is desirable for efficient photosynthesis that a photosynthetic reaction occur in an intermittent manner rather than continuous one. A modification to the reaction bath 100 is shown in FIG. 10 which is designed to meet such a demand.

Figure 10:
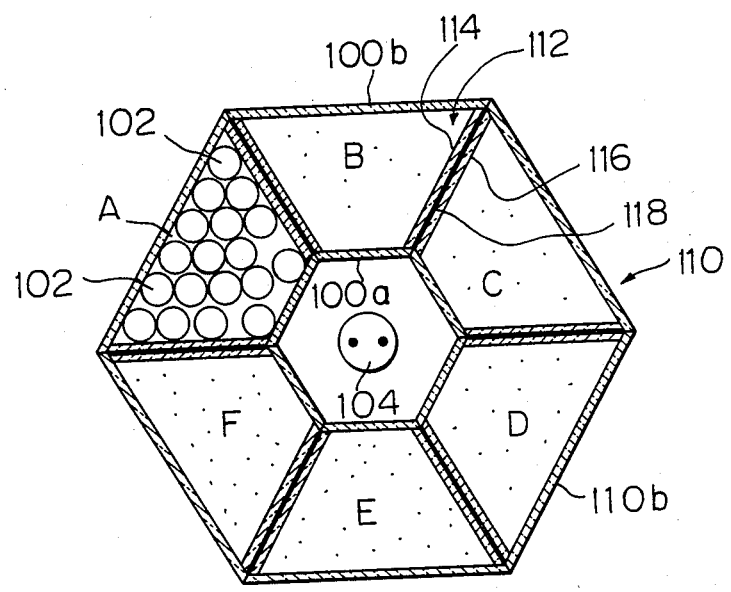
FIG. 10 is a sectional plan view of another embodiment of the present invention.

Referring to FIG. 10, the modified reaction bath, generally 110, comprises an inner wall 110a and an outer wall 110b which cooperate to define a generally annular space therebetween. The space between the walls 110a and 110b is divided into a plurality of compartments A, B, C, D, E and F by partitions 112 which are individually reflective for light. Each partition 112 is made up of two transparent plates 114 and 116, and a reflective layer 118 held between the transparent plates 114 and 116 to furnish the partition 112 with reflectivity. A plurality of photoradiators 102 are arranged side by side in each of the compartments A–F.

With the construction shown in FIG. 10, the apparatus is capable of promoting efficient use of light reached the reaction bath for photosynthesis. An arrangement may be made such that the photosynthetic reaction occurs in some of the chambers A–F and not in the others (interruption of the supply of light and $CO_2$-containing air), the reacting and non-reacting chambers being sequentially switched. The adjacent compartments A–F may be intercommunicated at upper and lower portions thereof so that in any of the compartments which the rotor 56 has reached the culture medium and $CO_2$ are moved upwardly and then downwardly via the adjacent compartment. This will insure smooth circulation of the culture medium and $CO_2$.

Although the particular construction of the partition 112 shown and described is only illustrative, such is advantageous over others due to the greater ease of production, capability of preventing the reflective layer from being damaged by the culture medium or the like, and, therefore, significant durability.

Figure 11:
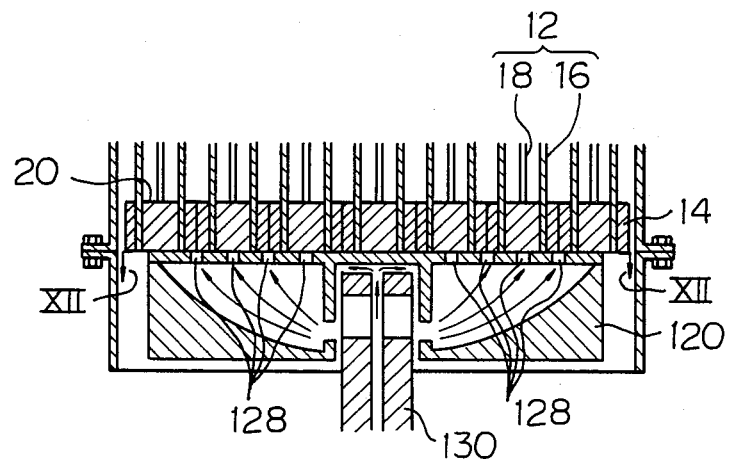
FIG. 11 is a fragmentary sectional view of a modification to the construction shown in FIGS. 11 and 12.
Figure 12:
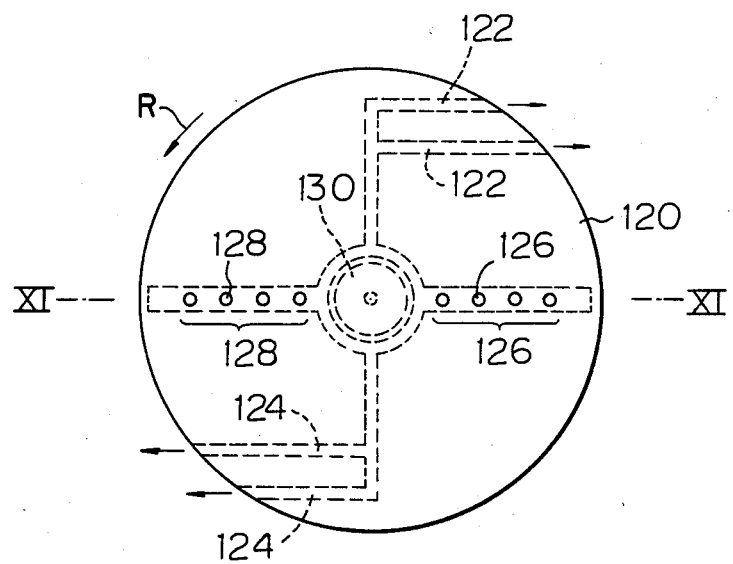
FIG. 12 is a plan view as seen in a direction XII—XII.

Referring to FIGS. 11 and 12, another embodiment of the present invention is shown. The apparatus in FIGS. 11 and 12 includes a rotatable disc 120 formed with horizontal air ejection passageways 122 and 124 and vertical air ejection passageways 126 and 128. The disc 120 is born and cushioned by $CO_2$-containing air which is fed under pressure to a conduit 130, which is configured similarly to previously mentioned conduit 26'. The illustrated construction of the apparatus above the disc 120 is essentially the same as the construction of the prior art apparatuses and, therefore, the same structural elements are designated by the same reference numerals. The disc 120 is rotated as indicated by an arrow R in FIG. 12 by the jets of air ejected from the passageways 122 and 124 while, at the same time, the air ejected from the vertical passageways 126 and 128 is routed into the reaction bath through the gaps between the adjacent photoradiators 12.

The disc 120 is advantageous over the prior art rectangular rotor 56 because it maintains the whole arrangement in a well-balanced condition and promotes positive and stable supply of $CO_2$-containing air into the reaction bath. Also, the disc 120 serves to effectively dissipate the culture medium from therebelow toward the reaction bath. The upper part of the apparatus including the reaction bath and the lower part including the disc may be detachably assembled as illustrated, so that the apparatus may be readily produced and maintained.

Figure 13:
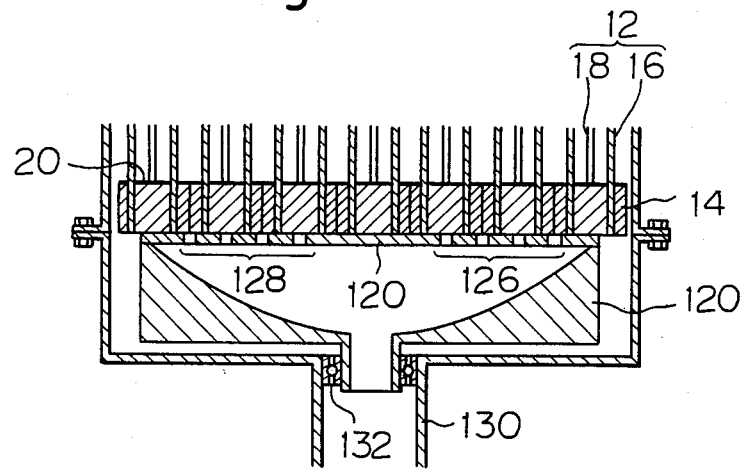
FIG. 13 is a fragmentary section of a modification to the construction shown in FIGS. 11 and 12.

A modification to the apparatus described with reference to FIGS. 11 and 12 is shown in FIG. 13. A characteristic feature of the modified apparatus is that the rotary disc 120 is supported by the conduit 130 through an air-tight bearing 132. Such a bearing construction will add to the stability of rotation of the disc 120.

Figure 14:
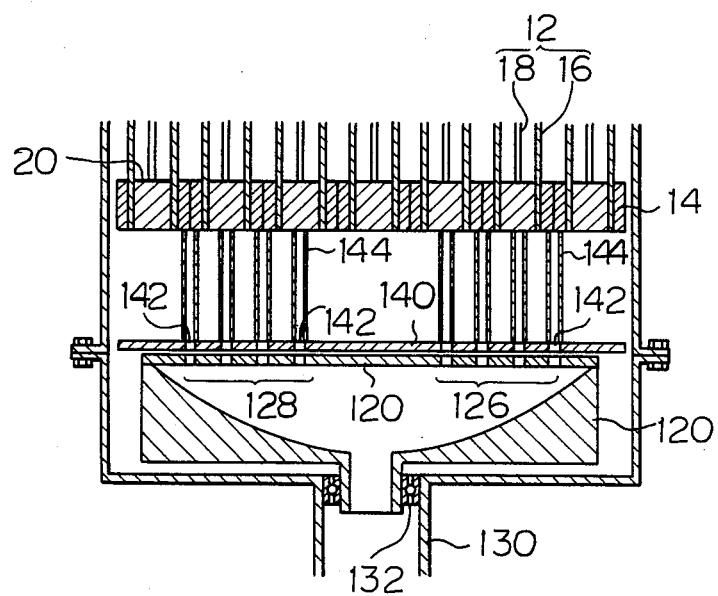
FIG. 14 is a fragmentary section of another embodiment of the present invention.
Figure 15:
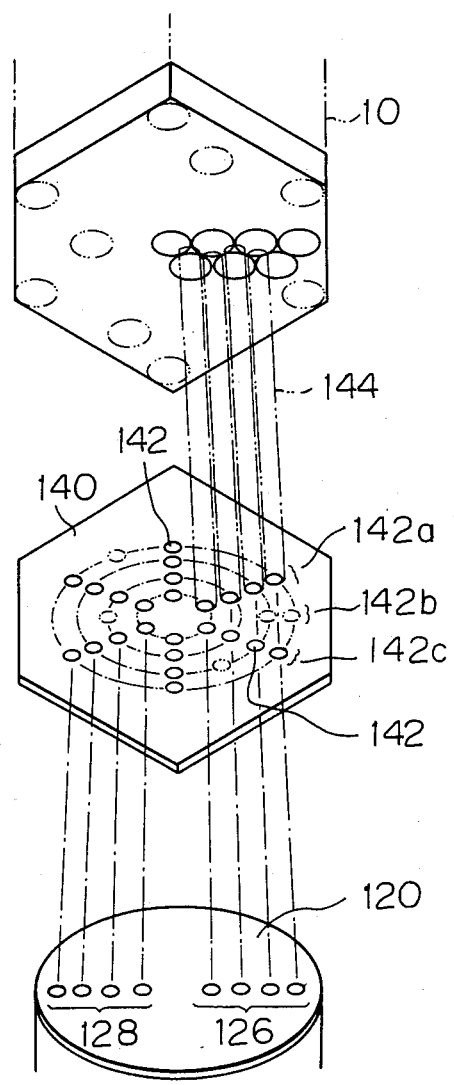
FIG. 15 is an exploded view of the embodiment shown in FIG. 14.

Referring to FIGS. 14 and 15, another embodiment of the present invention is shown which includes the disc support construction shown in FIG. 13 and a unique conduitwork for the supply of $CO_2$-containing air from the disc 120 to the reaction bath. In FIGS. 14 and 15, the same or similar structural elements as those of the previous embodiments are designated by the same reference numerals.

In FIGS. 14 and 15, the apparatus comprises a plate 140 formed with apertures 142 at predetermined positions which will be described, and tubes 144 adapted to respectively connect the apertures 142 in the plate 140 to the gaps 28 (FIG. 3) between the adjacent photoradiators. The disc 120 is located below the apertured plate 140 and rotatably supported by the fluid-tight bearing 132.

As shown in detail in FIG. 15, a plurality of radial arrays of apertures 142 are positioned in the plate 140 such that the apertures 142 in each radial array are registered with those in the other arrays on concentric circles. Each aperture 142 is communicated to a gap 28 between adjacent photoradiators by one of the tubes 144. Further, the apertures 142 in each radial array are located such that they will register with the vertical passageways 126 or 128 in the disc 120 when the latter arrive thereat.

In the construction shown in FIGS. 14 and 15, the disc 120 rotating in a predetermined direction brings its vertical passageways 126 and 128 into register with the aperture arrays sequentially, e.g., aperture arrays 142*a*, 142*b*, 142*c* . . . $CO_2$-containing air is routed through the aligned holes into the tubes 144 and, therefrom to the gaps 28 corresponding to the specific aperture array. In accordance with the rotation of the disc 120, the position to which the $CO_2$-containing air is supplied is changed every moment.

It will be apparent to those skilled in this art that the partitioned reaction bath design described with reference to FIG. 10 is also applicable to the embodiment shown in FIGS. 14 and 15 in order to achieve smaller pneumatic resistance and, thereby, smoother supply of $CO_2$-containing air.

Figure 16:
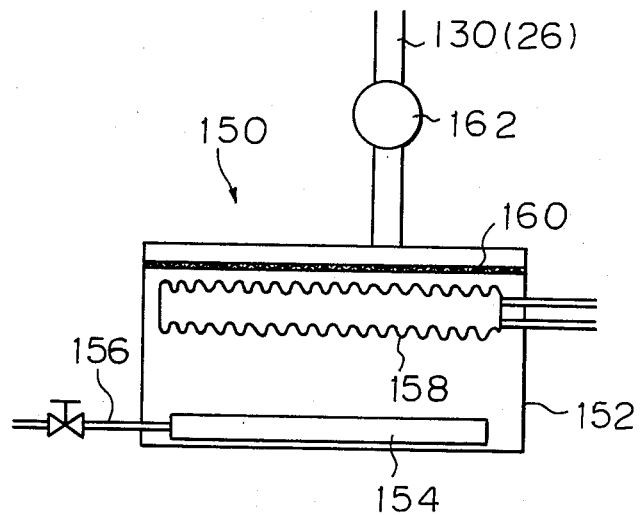
FIG. 16 is a schematic view of a device for producing $CO_2$-containing air associated with the apparatus of the present invention.

Referring to FIG. 16, a source of $CO_2$-containing air supply in accordance with the present invention is shown. The source of air supply, generally 150, comprises a housing 152 the interior of which is communicated to the conduit 130 (26). A burner 154 for burning any kind of hydrocarbon gas such as natural gas or propane is disposed in the housing 152 and communicated to a gas supply (not shown) by a valved piping 156. Located above the burner 154 is a heat exchanger 158. A filter 160 for filtering dust is positioned above the heat exchanger 158. When the hydrocarbon gas is burned by the burner 154, $CO_2$ and water are produced in the housing 152. A pump 162 compresses the $CO_2$ to feed it under pressure to the reaction bath via the conduit 130 (26).

As previously discussed, the intermittent photosynthesis mode is more desirable than the continuous photosynthesis mode. While photosynthesis is interrupted, it is necessary to supply oxygen to the desired substance in the reaction bath. Such oxygen supply is readily attainable with the device shown in FIG. 16, that is, merely by interrupting the combustion of the gas in the housing 152. As such, $CO_2$ and oxygen can be switched with ease from one to the other.

The heat exchanger 158 in the housing 152 serves to prevent hot air in the housing 152 from being communicated to the reaction bath. If desired, the heat exchanger 158 may bifunction to prevent cool air from being communicated to the reaction bath while the photosynthetic reaction is interrupted, so that air can be supplied constantly at an optimum temperature to the reaction bath to further enhance the efficiency of photosynthesis.

In summary, it will be seen that the present invention provides an apparatus for photosynthesis which effectively and stably supplies light and $CO_2$-containing air into a reaction bath to promote efficient photosynthetic reactions. The apparatus is furnished with an economical and simple device for the supply of $CO_2$-containing air. In an intermittent photosynthesis mode, carbon dioxide and oxygen can be alternately supplied with ease. Combustion of hydrocarbon gas in accordance with the present invention serves to kill germs in the air before the air is supplied to the housing 152.

Various modifications will become possible for those skilled in the art after receiving the teachings of the present disclosure without departing from the scope thereof. For example, while the embodiments shown in FIGS. 11-15 have employed the reaction bath and photoradiator arrangement of the applicant's previously proposed apparatuses, use may naturally be made of the generally annular construction discussed with reference to FIGS. 6-10.

What is claimed is:

1. An apparatus for photosyntheses comprising:
   a reaction bath means for causing a photosynthetic reaction therein, said reaction bath means comprising an inner transparent wall and an outer transparent wall surrounding and spaced from said inner transparent wall to define an annular space between the inner and the outer transparent walls, the inner and outer transparent walls being generally vertically disposed, and a light source positioned radially inwardly of the inner wall;
   a plurality of narrow tubular photoradiators arranged upright in said annular space parallel to each other, each of said photoradiators being constructed to radiate light which propagates therethrough; and
   a disc rotatable in a horizontal plane below the reaction bath means and disposed perpendicular to the photoradiators to eject jets of carbon dioxide-containing air into the annular space.

2. An apparatus as claimed in claim 1, in which the reaction bath means comprises reflector plates for separating said annular space into a plurality of compartments.

3. An apparatus as claimed in claim 1, in which said reaction bath means further comprises coaxial inner and outer tubes around the light source.

4. An apparatus as claimed in claim 3, in which an annular space is defined between the inner and outer tubes, and a material in the last said annular space which absorbs infrared rays.

5. An apparatus as claimed in claim 4, in which said material comprises water.

6. An apparatus as claimed in claim 1, further comprising carbon dioxide gas supply means for supplying carbon dioxide gas to the reaction bath means via the rotatable disc, said carbon dioxide gas supply means comprising a burner for burning hydrocarbon gas to produce the carbon dioxide gas and water.

7. An apparatus as claimed in claim 6, in which the carbon dioxide gas supply means further comprises a heat exchanger through which the carbon dioxide gas is delivered to the reaction bath means.

8. An apparatus as claimed in claim 6, in which said carbon dioxide gas supply means further comprises a filter through which the carbon dioxide gas is delivered to the reaction bath means.

9. An apparatus as claimed in claim 6, in which the carbon dioxide gas supply means is activated during photosynthetic reaction in said reaction bath means to feed carbon dioxide-contaiing air under pressure to the reaction bath means and deactivated during a suspension of the photosynthetic reaction to allow natural air to be fed under pressure to the reaction bath means.

10. An apparatus as claimed in claim 2, wherein the plurality of compartments are connected such that fluid flow through the plurality of compartments is serial.

11. An apparatus for photosynthesis comprising:
a reaction bath for causing a photosynthetic reaction therein;
a plurality of narrow tubular photoradiators arranged upright in said reaction bath parallel to each other and with gaps therebetween, each of said photoradiators being constructed to radiate light which propagates therethrough; and
a disc rotatable in a horizontal plane below and perpendicular to the photoradiators, said disc being formed with horizntal passageways for ejecting jets of carbon dioxide-containing air, and vertical passageways for ejecting jets of carbon dioxide-containing air toward said gaps between the adjacent photoradiators, said horizontal passageways being oriented to apply a moment of a force which tends to rotate the disc about its axis, whereby the disc is caused to rotate while supplying the carbon dioxide-containing air into the reaction bath via the vertical passageways.

12. An apparatus as claimed in claim 11, further comprising air bearing means which causes the disc to be supported by the carbon dioxide-containing air.

13. An apparatus as claims in claim 11, further comprising an air-tight bearing for supporting the disc.

14. An apparatus as claimed in claim 11, further comprising an apertured plate formed with a plurality of apertures and located in a horizontal plane between the photoradiators and the rotatable disc, and a plurality of tubes each communicating any of the apertures in the apertured plate to any of the gaps between the adjacent photoradiators.

15. An apparatus as claimed in claim 14, in which the vertical passageways in the rotatable disc are sequentially brought into register with the apertures in the apertured plate while the disc is rotated.

16. An apparatus as claimed in claim 15, in which the apertures in the apertured plate are positioned in a plurality of radially extending arrays and on a plurality of concentric circles, the vertical passageways in the disc sequentially registering with at least one of the radial aperture arrays in the apertured plate at a time.

17. An apparatus as claimed in claim 16, in which the reaction bath comprises partition means for partitioning the reaction bath into compartments which correspond to the radial aperture arrays in the apertured plate respectively, the gaps between the adjacent photoradiators in each of the compartments corresponding to any of the radial aperture arrays.

18. An apparatus as claimed in claim 11, further comprising carbon dioxide gas supply means for supplying carbon dioxide gas to the reaction bath via the rotatable disc, said carbon dioxide gas supply means comprising a burner for burning hydrocarbon gas to produce the carbon dioxide gas and water.

19. An apparatus as claimed in claim 18, in which the carbon dioxide gas supply means further comprises a heat exchanger through which the carbon dioxide gas is delivered to the reaction bath.

20. An apparatus as claimed in claim 18, in which the carbon dioxide gas supply means further comprises a filter through which the carbon dioxide gas is delivered to the reaction bath.

21. An apparatus as claimed in claim 18, in which the carbon dioxide gas supply means is activated during photosynthetic reaction in the reaction bath to feed the carbon dioxide-containing air under pressure to the reaction bath and deactivated during suspension of the photosynthetic reaction to allow natural air to be fed under pressure to the reaction bath.

* * * * *